United States Patent [19]
Choi

[11] Patent Number: 4,806,543
[45] Date of Patent: Feb. 21, 1989

[54] METHOD AND COMPOSITIONS FOR REDUCING NEUROTOXIC INJURY

[75] Inventor: Dennis W. Choi, Stanford, Calif.

[73] Assignee: Board of Trustees of the Leland Stanford Junior University, Stanford, Calif.

[21] Appl. No.: 934,733

[22] Filed: Nov. 25, 1986

[51] Int. Cl.⁴ ............................................. A61K 31/36
[52] U.S. Cl. .................................. 514/464; 514/465; 514/466
[58] Field of Search ....................... 514/464, 465, 466

[56] References Cited

PUBLICATIONS

De Sterons, Medicinal Chemistry, vol. 5, Analgesics (1985) pp. 144–145.
Church et al., Eur. J. Pharmacol. (1985) 111:185–190.
Rothman, J. Neurosci. (1984) 4:1884–1891.
Simon et al., Science (1984) 226:850–852.
Weiloch, Science (1985) 230:681–683.
Choi et al., Soc. Neurosci. Abs. (1986) 12:381.
Isbell et al., J. Pharmacol. Exp. Therap. (1953) 107:524–530.
Jaffe and Martin, "Opioid Analgesics and Antagonists", Goodman and Gillman's Pharmacological Basis of Therapeutics, Alfred Goodman Gillman et al., eds., 7th Edition, 1985, MacMillan and Company, New York, pp. 491–531.

Primary Examiner—Stanley J. Friedman
Attorney, Agent, or Firm—Richard L. Neeley

[57] ABSTRACT

A method for reducing adverse effects of neurotoxic injury, which comprises administering to a patient susceptible to neurotoxic injury an effective amount, sufficient to reduce the injury, of a compound which is an enantiomer of an analgesic opioid agonist or antagonist, preferably an opiate agonist having a ring system of the following stereochemistry, which shows only carbon and nitrogen atoms in the rings:

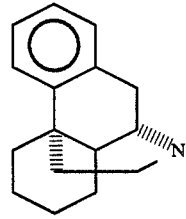

The dextrorotatory opiates, dextrorphan and dextromethorphan, are particularly suitable for use in the method of the invention.

17 Claims, No Drawings

METHOD AND COMPOSITIONS FOR REDUCING NEUROTOXIC INJURY

BACKGROUND OF THE INVENTION

1. Field of the Invention

The present invention is in the field of pharmacology and specifically relates to the new use of enantiomers of morphine-like opioids, a known class of compounds, to protect central neurons from neurotoxic injury.

2. Description of the Background

The brain is exquisitely sensitive to brief hypoxia, while other tissues may survive during hypoxia for extended periods. Recently, attention has been focused on a possible role of the excitatory neurotransmitter glutamate, or related compounds, in the pathogenesis of the neuronal injury scene with a variety of brain insults, including hypoxia. Glutamate both is present at high concentrations in the mammalian central nervous system (CNS) and is toxic to central neurons. Evidence for a role of glutamate in mediating hypoxic neuronal injury is shown by the fact that certain glutamate antagonists can attenuate the acute neuronal injury produced by hypoxia, ischemia, and hypoglycemia.

The observed protective effects of glutamate antagonists on central neurons have raised the possibility that such drugs might have clinical therapeutic utility in hypoxic brain injury. However, the drugs previously known are not currently available from a clinical standpoint (e.g., have not undergone clinical trials), and little is known of their systemic effects. Furthermore, glutamate is known to be a broad-spectrum agonist with efficacy at three subtypes of excitatory amino acid receptors—kainate, quisqualate, and N-methyl-D-aspartate (NMDA). Prior to the present invention, it was not known whether blockade at one, a combination of two, or all three of the receptor subtypes was necessary to block the neurotoxicity of glutamate.

Accordingly, there remains a need for identification of pharmacologically active compounds capable of interacting with glutamate receptors to produce the desired protective effect.

Relevant Publications

Church and colleagues have reported that the dextrorotatory morphinan opioid dextrorphan blocks the excitation of spinal neurons induced by application of NMDA, but not by kainate or quisqualate (Church, J., et al. (1985), "Differential Effects of Dextrorphan and Levorphanol on the Excitation of Rat Spinal Neurons by Amino Acids", *Eur. J. Pharmacol.*, 111:185–190). The study did not rule out indirect explanations (e.g., presynaptic effects) for the observed alteration in NMDA excitation. Various investigators have studied the relationship of glutamate antagonists to hypoxia (Rothman, S. (1984), "Synaptic Release of Excitatory Amino Acid Neurotransmitter Mediates Anoxic Neuronal Death", *J. Neurosci.*, 4:1884–1891), ischemia (Simon, R. P., et al. (1984), "Blockade of N-methyl-B-aspartate Receptors May Protect Against Ischemic Damage in the Brain", *Science*, 226:850–852), and hypoglycemia (Weiloch, T. (1985), "Hypoglycemia-Induced Neuronal Damage Prevented by an N-methyl-D-aspartate Antagonist", *Science*, 230:681–683). An abstract which reports preliminary investigations of the inventor is Choi. D. W., et al. (1986), "Glutamate Neurotoxicity in Cortical Cell Culture is Attenuated by N-methyl-D-aspartate Receptor Antagonists", *Soc. Neurosci. Abs.*, 12:381.

Pharmacology of dextrorphan and dextromethorphan is discussed in Isbell, H. and Fraser, H. F., (1953) "Actions and Addiction Liabilities of Dromoran Derivatives in Man", *J. Pharmacol. Exp. Therap.*, 107:524–530.

SUMMARY OF THE INVENTION

The present invention provides a method for reducing the adverse effects of neurotoxic injury by administering to a patient susceptible to neurotoxic injury an amount, sufficient to reduce neurotoxic effects caused by glutamate, of a compound which is an enantiomer of an analgesic opioid agonist or antagonist, preferably a dextrorotatory opiate agonist having a ring system with the following stereochemistry (in which only ring carbon and nitrogen atoms are shown):

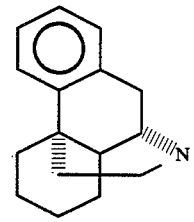

Dextrorphan and dextromethorphan are particularly suitable for use in the present invention.

DESCRIPTION OF SPECIFIC EMBODIMENTS

The present invention has arisen out of the finding that enantiomers of classical morphine-like opioids are useful in preventing or reducing the adverse effects of neurotoxic injury caused by release of glutamate from cells. Preferred compounds are dextrorotatory enantiomers of morphine-like opiates (especially morphinans) having a ring structure in which the 3-dimensional arrangement of the rings is a mirror image of the ring arrangement in morphine. Opioid here is used in the generic sense to refer to all drugs, natural and synthetic, with morphine-like actions. The term opiate is used to designate drugs derived from opium—morphine, codeine, and the many semi-synthetic congeners of morphine—that have a morphinan ring system. Morphine is a pentacyclic opiate having the ring and numbering system set forth below:

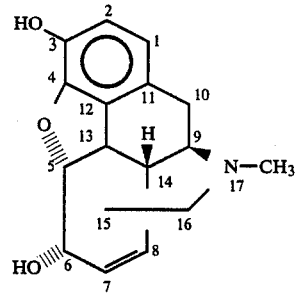

There is a considerable amount of confusion in the scientific literature regarding the correct absolute stereochemistry of morphine and dextromethorphan. A number of secondary literature references (texts, compilations of data, and review articles) show morphine as being the enantiomer of the structure set forth above. However, it is not clear in all cases whether the intention of the publication is to show absolute or relative stereochemistry. The absolute stereochemistry set forth in this specification is based on a comprehensive review of the stereochemistry of the morphine alkaloids in *Chemistry of Carbon Compounds*, E. H. Rodd, ed. Vol. IVC, Elsevier Publishing Co., New York, 1960, pp 2081–2083. Clearly, morphine as isolated from the poppy plant has a specific absolute stereochemistry, and it is this stereochemistry that is intended. The same is true for the dextrorotatory enantiomer of racemorphan (i.e., the compound known as dextrorphan) and its methyl ether (dextromethorphan).

Since the prior art has been interested in mimicking morphine without adverse side effects or in producing an antagonist that interacts with the same receptors as morphine, considerable research has been carried out into compounds having morphine-like analgesic and sedative activity. Accordingly, compounds useful in the practice of the present invention can readily be defined in terms of the known opioids and opiates. The present invention is directed to the use of compounds that have an enantiomeric (mirror image) relationship to known opioids having morphine-like activity.

Those compounds having opioid character and a morphine-type ring system have the same stereochemistry of the ring system as morphine (i.e., they are levorotatory). For example, codeine is methylmorphine, the methyl substitution occurring on the phenolic hydroxy group. Antagonists of morphine, such as naloxone, also have the same ring stereochemistry. A number of morphine-like opiates and opiate antagonists are set forth in Table 1.

tory depression, etc.) are so severe that such use is impractical. However, the present inventor has discovered that enantiomers of the known opioid analgesics, which do not give rise to morphine-like effects, are capable of protecting central nervous system neurons against toxic injury caused by release of glutamate.

The relationship of enantiomers to each other is that of an object and its mirror image. Because of the three dimensional nature of a binding reaction of a compound and its receptor, the enantiomer of a compound having biological activity is often inactive because it cannot bind with the receptor of the active molecule.

Enantiomers are traditionally referred to by their ability to rotate polarized light as either being dextrorotatory or levorotatory. However, although compounds with similar stereochemistry typically rotate light in the same direction, it is possible that the substitution of one functional group for another without changing, as in this case, the basic ring structure stereochemistry, will result in a different rotation of light. Accordingly, in the present application compounds of the invention are defined by their being a mirror image (enantiomer) of an analgesic opioid agonist or antagonist since this is more precise than by referring to the physical ability of such molecules to rotate polarized light in a particular direction. Nevertheless, compounds having a ring structure with the stereochemistry of morphine are typically levorotatory. Accordingly, dextrorotatory opiates represent preferred compounds for use in the method of the present invention. It will be realized that certain opioid compounds (which may not have the same ring structure) may rotate polarized light either in a dextrorota-

TABLE 1

Structures of Opioids and Opioid Antagonists Chemically Related to Morphine

| Nonproprietary Name | Chemical Radicals and Positions | | | Other Changes+ |
|---|---|---|---|---|
| | 3* | 6* | 17* | |
| Agonists | | | | |
| Morphine | —OH | —OH | —CH$_3$ | — |
| Heroin | —OCOCH$_3$ | —OCOCH$_3$ | —CH$_3$ | — |
| Hydromorphine | —OH | =O | —CH$_3$ | (1) |
| Oxymorphone | —OH | =O | —CH$_3$ | (1),(2) |
| Levorphanol | —OH | —H | —CH$_3$ | (1),(3) |
| Levallorphan | —OH | —H | —CH$_2$CH=CH$_2$ | (1),(3) |
| Codeine | —OCH$_3$ | —OH | —CH$_3$ | — |
| Hydrocodone | —OCH$_3$ | =O | —CH$_3$ | (1) |
| Oxycodone | —OCH$_3$ | =O | —CH$_3$ | (1),(2) |
| Antagonists | | | | |
| Nalorphine | —OH | —OH | —CH$_2$CH=CH$_2$ | — |
| Naloxone | —OH | =O | —CH$_2$CH=CH$_2$ | (1),(2) |
| Naltrexone | —OH | =O | —CH$_2$— | (1),(2) |
| Buprenorpphine | —OH | —OCH$_3$ | —CH$_2$— | (1),(2),(4) |
| Butorphanol | —OH | —H | —CH$_2$— | (2),(3) |
| Nalbuphine | —OH | —OH | —CH$_2$— | (1),(2) |

*The numbers 3, 6, and 17 refer to positions in the morphine molecule, as shown above.
+Other changes in the morphine molecule are as follows:
(1) Single instead of double bond between C7 and C8.
(2) OH added to C14.
(3) No oxygen between C4 and C5.
(4) Endoetheno bridge between C6 and C14; 1-hydroxy-1,2,2-trimethylpropyl substitution on C7.

The structure and activity of these and other opioid analgesic agonists and antagonists are discussed in Jaffe and Martin, "Opioid Analgesics and Antagonists", Goodman and Gillman's Pharmacological Basis of Therapeutics, Alfred Goodman Gillman et al., eds., 7th Edition, 1985, MacMillan and Company, New York, pps. 491–531.

Although morphine-like compounds may be effective in protecting neural cells against the effects of glutamate, the adverse effects (addiction, sedation, respiratory or levorotatory fashion.

The major advantage of dextrorotatory opiates over conventional levorotatory opiate agonists and antagonists is twofold: (1) greater anti-neurotoxic potency and (2) virtual absence of interaction with conventional opioid $\mu$ or $\kappa$ receptors. This advantage allows high dose levels of compounds of the invention to be used without complicating interactions at the $\mu$ or $\kappa$ morphine receptors.

While levorotatory opiate agonists and antagonists also have some (but lesser) ability to block glutamate neurotoxicity, the actions of these levorotatory compounds at conventional μ or κ receptors will produce severely limiting complications: morphine-like narcotic effects including respiratory depression (in the case of agonists) and blockade of analgesia (in the case of antagonists).

Opiates useful in the practice of the present invention will typically have a morphinan ring system. The stereochemistry of a morphinan ring system that is in an enantiomeric relationship to that of morphine is shown below:

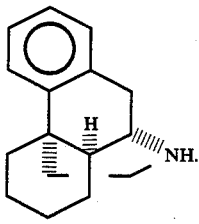

The compound shown is morphinan itself. Compounds of the invention having a morphinan-like ring will typically have substituents of the type shown in Table 1 above and in morphine itself.

The best known morphinan having its ring stereochemistry opposite to that of morphine is dextromethorphan, also known by its chemical name of (+)-3-methoxy-N-methyl morphinan. As indicated by its name, dextromethorphan is the dextrorotatory isomer and has the following structure and stereochemistry:

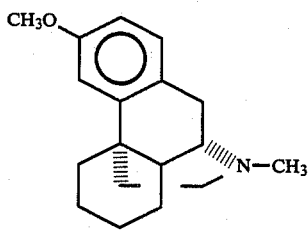

Another well known morphinan of opposite stereochemistry to morphine is dextrorphan, which is (+)-3-hydroxy-N-methylmorphinan. Levorphanol, the corresponding (−)-isomer of dextrorphan, is an active morphine-like compound. These and a number of related compounds are disclosed in U.S. Pat. Nos. 2,676,177 and 2,744,112, dating from 1954 and 1956, respectively.

Dextromethorphan and dextrorphan are particularly preferred compounds as they have been approved for oral clinical use in humans in the form of cough suppressants and other cold remedies, many of which are available in over-the-counter products without a perscription.

According to the standard Gillman and Goodman's text cited above, dextromethorphan and dextrorphan, unlike their enantiomers, have no analgesic or addictive properties. These compounds act centrally to elevate the threshhold for coughing. Compared to codeine, which is also useful as a cough suppressant but which has morphine-like addictive and analgesic effects, dextromethorphan produces fewer subjective and gastrointestinal side effects.

In addition to morphine-like opiates, other opioids that have an enantiomeric relationship to an opioid having morphine-like characteristics may be effective. Such compounds would be enantiomers of opioids such as endogenous opioid peptides (enkephalins, endorphins, and dynorphins), phenylpeperadine analgesics (neperidine and related compounds), methadone and congeners, agonist/antagonists, and partial agonists (pentazocine and related compounds), and opioid antagonists (naloxone and related compounds). Compounds having a morphine-like bridged ring system, most preferably a morphinan ring system, are preferred.

Because of the relationship of lipophilicity to ability of a molecule to pass the blood-brain barrier, more highly lipophilic opiates and opioids are preferred over compounds of similar structure but less lipophilic character. For example, compounds containing hydroxyl groups are less preferred than the corresponding lower alkyl ethers and lower alkanoyl esters. Methyl ethers and acetyl esters are useful for this purpose.

The compounds of the invention can be utilized to protect against a number of neurotoxic injuries caused by the action of excess glutamate or related compounds on central neurons. There is a considerable body of evidence indicating that the neurotoxicity of the endogenous excitatory amino acid glutamate (and/or related endogenous compounds, including quinolinate, homocysteate, and aspartate) play a critical role in the pathogenesis of central neuronal injury in the setting of several acute and chronic neurological diseases, including ischemia, hypoxia, hypoglycemia, epilepsy, Huntington's disease, and Alzheimer's disease. Glutamate is typically released from cells when insufficient energy is available for the cells to maintain their normally high internal glutamate concentrations. High internal glutamate concentrations are maintained by an active transport system that utilizes energy. Under low energy conditions, such as during ischemia, hypoxia, or hypoglycemia, glutamate is released by the cells. Release of glutamate stimulates further release of glutamate, resulting in a cascade of neurotoxic damage.

Experimental work in the laboratory of the inventor has established a cortical cell culture model system capable of accessing neuronal cell injury. Using this system it has been demonstrated that glutamate is a much more potent neurotoxin than previously believed. Additional experimental evidence in the inventor's laboratory has indicated that blockade of only one of the three subclasses of glutamate receptors is necessary to systematically convey neuronal resistance to both glutamate neurotoxicity and to hypoxic injury.

Dextrorphan is somewhat more potent than its levorotatory isomer levorphanol at blocking glutamate neurotoxicity. Levorphanol is several orders of magnitude more potent than dextrorphan at classic (i.e., morphine or μ-κ-δ) opiate receptors. This evidence experimentally confirms that these morphinans are acting in a non-classical fashion to block glutamate neurotoxicity and are not behaving in a manner consistent with their normal use as cough suppressants.

The fact that these drugs act selectively to block neurotoxicity only at the one subclass of glutamate receptors means that the desired goal of neurotoxic blockade and protection against the effects of glutamate can be accomplished with the least number of side effects. Accordingly, there is less disruption of normal brain function utilizing compounds of the invention than when utilizing other types of glutamate antagonists, such as kynurenate, which acts broadly on all three subclasses of glutamate receptors. Additionally, dextromethorphan and dextrorphan are relatively free of side effects in humans. In particular, these drugs have little in the way of classic opiate effects including respiratory depression, euphoria, addiction, and sedation that might otherwise complicate the proposed use.

The method of the invention is carried out by administering to a patient susceptible to neurotoxic injury an amount of a compound of the invention sufficient to reduce neurotoxic effects. If necessary, any residual morphine-like side effects can be blocked by co-administration of a μ-κ receptor antagonists such as naloxone. The method is suitable for use in any animal species having N-methyl-D-aspartate receptors. The term patient is intended to include any such animal to which a compound of the invention would be administered for the indicated purpose, including both medicinal and veterinary uses. Use in mammals and birds of all types is preferred, with use in humans being a primary utility.

Administration can be by any technique capable of introducing the compounds of the invention into the blood stream of the patient, including oral administration and intravenous, intramuscular, and subcutaneous injections. Preparation of opiates for administration to patients, particularly humans, is well known and can be applied directly to administration of the compounds of the present invention.

Some compounds of the invention, such as dextromethorphan, have been formulated in orally administratable forms for use as cough suppressants. Such formulations could be used in the practice of the present method but are not preferred. If a composition containing dextromethorphan or another opioid of the invention is utilized as an orally acceptable composition, it is preferred to have higher concentrations than those that are present in the currently available formulations intended for use as cough syrups. Typical doses in orally acceptable pharmaceutical carriers would be from 50 mg to 2 g, preferably from 100 mg to 1 g. These doses are for administration to a typical 70-kg human. Administration can be adjusted to provide the same relative dose per unit of body weight.

A preferred formulation comprises a pharmacologically active dextrorotatory opiate and an inert carrier suitable for use as an injectable solution or suspension. Aqueous solutions, optionally containing minor amounts of an organic solvent, such as ethanol, for use in increasing solubility, are particularly preferred. Preferred is an injectable solution containing from 50 mg to 2 g, preferably from 100 mg to 1 g of the opiate. The amount utilized for any particular patient will vary depending on the body weight and particular use, as is well understood in the art. Typical concentrations in the blood stream on the order of 1–1000 micromolar, preferably 10–100 micromolar, will be useful.

Injectable formulations of the invention will differ from simple aqueous solutions in that they have been formulated for pharmaceutical use and therefore will not contain pyrogens and other substances that may be present in typical laboratory solutions of organic compounds.

All compounds of the invention can be made by standard techniques that are available for producing opioids and opiates. Totally synthetic syntheses of opiates have been reported. It is well known that synthetic procedures for synthesizing chiral compounds will give rise to both enantiomers (in the absence of special techniques, for example those involving reactants or catalysts that themselves are optically active). Enantiomers are generally resolved by forming a salt or other derivative of the enantiomers with an optically active compound. The resulting diastereomers have different physical properties and can be separated. Accordingly, compounds of the invention can be prepared utilizing the same techniques as those utilized to produce known opioids with selection of the enantiomer that is normally discarded when a morphine-like agonist or antagonist is being synthesized.

The following examples are provided for purposes of illustration only and are not to be considered limiting of the invention unless otherwise specified.

EXAMPLE

Mixed cortical cell cultures, containing both neuronal and glial elements, were prepared as previously described (Choi, D. W., *Neurosci. Lett.* (1985) 58:293–297) from fetal mice at 14–17 days gestation. Dissociated cortical cells were plated on collagen-coated 35 mm dishes (106 cells/dish) in Eagle's minimal essential medium (MEM - Earl's salts) supplemented with 10% heat-inactivated horse serum, 10% fetal bovine serum, glutamine (2 mM), glucose (21 mM), and bicarbonate (38 mM). Cultures were maintained at 37° C. in a humidified 9% $CO_2$ atmosphere. After 5–7 days in vitro, non-neuronal cell division was halted by 1–3 days of exposure to $10^{-5}$M cytosine arabinoside, and the cells were shifted into a maintenance medium similar to the plating media, but lacking fetal serum. Subsequent media replacement was carried out on a biweekly schedule. Under these conditions, neurons (phase-bright when viewed under a phase-contrast microscope and bearing extensive processes) form an extensive, synaptically active network on top of an astrocyte (glial-fibrillary-acidic-protein-containing) monolayer.

Exposure to glutamate was carried out at room temperature in a tris-buffered exposure solution (substituted for culture medium by triple exchange) with the following composition (in mM):NaCl 120, KCl 5.4, $MgCl_2$ 0.8, $CaCl_{12}$ 1.8, tris-Cl (pH 7.4 at 25° C.), glucose 15. After 5 minutes, the exposure solution was thoroughly replaced with culture medium (lacking serum) (effective dilution >600), and the dishes were returned to the culture incubator. Individual microscope fields (200 x) were photographed both before and after exposure to glutamate (the latter both with phase-contrast and with brightfield following a 5 minute incubation in 0.4% trypan blue dye), using an objective marker to assist field relocation.

Quantitative assessment of neuronal injury was accomplished by measuring the extracellular concentration of the cytosolic enzyme lactate dehydrogenase (LDH) released to the culture medium by damaged neurons. Control experiments showed that the spontaneous release of LDH was low, that the appearance of extracellular LDH correlated well with morphological evidence of neuronal injury, and that no LDH was released when glia alone were exposed to 0.5 mM glutamate for 5 minutes.

LDH was measured 2 days following glutamate exposure in the culture medium (lacking serum, and hence lacking intrinsic LDH) at room temperature using the method of Wroblewski and LaDue (Wroblewski, F. and LaDue, J. S., *Proc. Soc. Exp. Biol. Med.* (1955) 90:210–213). Samples of media (0.1 ml) were added to 2.3 μmoles of Na pyruvate and 0.2 mg of added NADH in 0.1 M KPO$_4$ buffer (pH 7.5 at 25°) (total volume 3 ml). The absorbance of the reaction mixture at 340 nm, an index of NADH concentration, was measured with a spectrophotometer at 2 second intervals: LDH concentration was then calculated from the slope of the absorbance curve, fit by linear regression to the linear (initial) portion of the curve, and corrected for temperature and light path. Accuracy of the assay was verified by periodic checks of a standard LDH enzyme solution (Sigma Enzyme Control 2-E).

Exposure of cortical cell cultures to 0.5 mM glutamate for 5 minutes resulted by the following day in disintegration of the majority of the neurons: many remaining neurons failed to exclude trypan blue dye. LDH measurements showed a substantial rise in extracellular enzyme compared with the background appearance of LDH in cultures not exposed to glutamate.

However, if 100 μM dextrorphan (supplied by the Addiction Research Foundation, Palo Alto, Calif.) was added to the glutamate exposure solution, both the morphological and the chemical evidence of glutamate neurotoxicity was markedly attenuated. Neurons protected by addition of dextrorphan excluded trypan blue dye and remained morphologically stable for at least several days. Reducing the dextrorphan concentration to 10 μM reduced this protective effect somewhat (partial glutamate neurotoxicity was noted): at a concentration of 1 μM, only a slight protective effect was found (two experiments). Exposure of cultures to 100 μM dextrorphan alone for 5 minutes produced no evidence of neuronal damage.

The related opioid dextromethorphan (Sigma) at 100 μM had a similar protective effect against glutamate neurotoxicity, attenuating both the morphological and chemical evidence of neuronal injury. Similar experiments have established that dextrorphan and dextromethorphan can block the neurotoxicity of NMDA but not quisqualate or kainate in the cortical cell cultures.

The present results indicate that dextrorotatory opiates can substantially reduce the vulnerability of cortical neurons in mixed cell cultures to damage by exposure to glutamate or other NMDA agonists.

All publications and patent applications cited in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for reducing adverse effects of toxic injury to central neurons, which comprises:
   administering to a patient susceptible to toxic injury an amount, sufficient to reduce said effects, of a compound which is a mirror-image enantiomer of an analgesic opioid agonist or antagonist.

2. The method of claim 1, wherein said compound is an enantiomer of an analgesic opiate agonist.

3. The method of claim 2, wherein said compound is a morphinan.

4. The method of claim 3, wherein said compound is a N-methyl-3-(hydroxy or alkoxy)morphinan.

5. The method of claim 1, wherein said compound is dextrorphan.

6. The method of claim 1, wherein said compound is dextromethorphan.

7. The method of claim 1, wherein said toxic injury associated with ischemia, hypoxia, hypoglycemia, epilepsy, Huntington's disease, or Alzheimer's disease.

8. The method of claim 1, wherein said patient is a human.

9. A method for reducing toxic injury to central neurons mediated by an endogenous excitatory amino acid, which comprises:
   administering to a patient susceptible to said toxic injury an amount, sufficient to reduce said injury, of a compound which is a mirror-image enantiomer of an analgesic opioid agonist or antagonist.

10. The method of claim 9, wherein said compound is a mirror-image enantiomer of an analgesic opiate agonist.

11. The method of claim 10, wherein said compound is a morphinan.

12. The method of claim 11, wherein said compound is a N-methyl-3-(hydroxy or alkoxy)morphinan.

13. The method of claim 9, wherein said compound is dextrorphan.

14. The method of claim 9, wherein said compound is dextromethorphan.

15. The method of claim 9, wherein said toxic injury results from ischemia, hypoxia, hypoglycemia, epilepsy, Huntington's disease, or Alzheimer's disease.

16. The method of claim 9, wherein said patient is a human.

17. A method of reducing toxic injury to central neurons associated with ischemia, hypoxia, hypoglycemia, epilepsy, Huntington's disease, or Alzheimer's disease, which comprises:
   administering to a patient susceptible to said toxic injury an amount, sufficient to reduce said injury, of a compound selected from the group consisting of (1) analgesic opioid agonists and antagonists and (2) mirror-image enantiomers of analgesic opioid agonists and antagonists.

* * * * *